United States Patent
Yokoyama et al.

(10) Patent No.: US 7,616,295 B2
(45) Date of Patent: Nov. 10, 2009

(54) BIOMETRIC IDENTIFICATION APPARATUS

(75) Inventors: Shingo Yokoyama, Yokohama (JP);
Tadayuki Abe, Ichinoseki (JP); Hiromi Sugo, Kanegasaki (JP); Shoichi Sato, Ebina (JP)

(73) Assignee: Hitachi Media Electronics Co., Ltd., Iwate-ken (JP)

( * ) Notice: Subject to any disclaimer, the term of this patent is extended or adjusted under 35 U.S.C. 154(b) by 313 days.

(21) Appl. No.: 11/668,069

(22) Filed: Jan. 29, 2007

(65) Prior Publication Data

US 2008/0037001 A1  Feb. 14, 2008

(30) Foreign Application Priority Data

Aug. 8, 2006  (JP) .............................. 2006-215193

(51) Int. Cl.
*G06K 9/74* (2006.01)
(52) U.S. Cl. ........................................ 356/71
(58) Field of Classification Search .................... 356/71
See application file for complete search history.

(56) References Cited

U.S. PATENT DOCUMENTS

| 6,816,605 | B2 | 11/2004 | Rowe et al. |
| 7,254,255 | B2 * | 8/2007 | Dennis ....................... 382/115 |

FOREIGN PATENT DOCUMENTS

| JP | 2003-331268 | 11/2003 |
| JP | 2005-046306 | 2/2005 |

* cited by examiner

*Primary Examiner*—L. G. Lauchman
*Assistant Examiner*—Amanda H Merlino
(74) *Attorney, Agent, or Firm*—Antonelli, Terry, Stout & Kraus, LLP.

(57) ABSTRACT

A biometric identification apparatus that can accurately and rapidly perform liveness detection with a simple structure.

The apparatus includes a plurality of light sources 102, 103, 106, and 107, each having a wavelength different from one another, for emitting light to a finger 200 as an object to be identified, and receivers 104 and 105 for detecting the light passing through the finger. The ratio of the light emitted from the light sources to the light detected with the receivers is obtained as transmittance. Determination in liveness detection is made by comparing the transmittance with a previously-set threshold of transmittance.

4 Claims, 13 Drawing Sheets

BIOMETRIC IDENTIFICATION APPARATUS

FIELD OF THE INVENTION

The present invention relates to a biometric identification apparatus.

DESCRIPTION OF THE RELATED ART

A biometric identification technology based on biometric characteristics (fingerprints, veins, irises, etc.) of an individual has been proposed in many forms as means for identity verification. For example, the technology is used in automated teller machines (ATMs) of banks, and is used for access control to a controlled area. In addition, the technology is used when a person logs on a computer.

Basically, the identity verification using a biometric identification apparatus is done by registering, in advance, biometric information of an individual to be identified, followed by a matching process with the stored information. There is apprehension, however, that a possible fraudulent impostor who steals the registered information to create a sophisticated imitation of a living body (a spoof of finger, iris, or the like) using the stolen information, may disguise him or herself as an individual who he/she claims to be.

In view of such apprehension, Patent Documents 1 and 2, for example, disclose biometric identification apparatus that prevents such a masquerade. Specifically, according to the method, a temporally-continuous series of images of veins are photographed, and changes in luminance values of the images are associated with a pulse of an object to be identified, so as to determine whether the object is a living finger or a spoof thereof.

[Patent Document 1] JP Patent publication (Kokai) No. 2003-331268 A

[Patent Document 2] JP Patent Publication (Kokai) No. 2005-46306 A

SUMMARY OF THE INVENTION

Problems to be Solved by the Invention

However, such pulse detection methods as disclosed in JP Patent Publication (Kokai) No. 2003-331268 A and JP Patent Publication (Kokai) No. 2005-46306 A have the following problems. Specifically, since a signal of the pulse itself is minute, it is difficult to accurately separate the pulse from other noise. Moreover, a low blood-flow rate in a cold environment makes it even more difficult to detect the pulse. In short, the accuracy of the method tends to depend on the surrounding environment.

An object of the present invention is to provide a biometric identification apparatus capable of accurately and rapidly performing liveness detection with a simpler structure than that of conventional technology, by focusing on inherent transmittance of a living body, not on a feeble, dynamic signal such as a pulse.

MEANS OF SOLVING THE PROBLEMS

The aforementioned object can be achieved as follows. A finger placement portion in which a finger is placed, a first, a second and a third light source each having a different wavelength from one another for emitting light to the finger, and a receiver for detecting light passing through the finger are provided. The transmittance; that is, the light intensity ratio of the light emitted from each of the first, the second and the third light source to the light detected with the receiver, is obtained. Determination in liveness detection on the finger is made by comparing the transmittance with respective previously-set transmittance thresholds. Thereafter, a detection result is displayed.

Additionally, in order to achieve the aforementioned object, the first and the second light source are disposed so that the optical axes of the first and the second light source form lines perpendicular to the bottom surface of the finger placement portion. The third light source is disposed so that the optical axis of the third light source is parallel to the bottom surface of the finger placement portion and perpendicular to the optical axes of the first and the second light source. A receiving surface of the receiver is disposed parallel to the bottom surface of the finger placement portion.

Additionally, in order to achieve the aforementioned object, the wavelengths of the first, the second and the third light source include a visible light region and a near-infrared light region.

Additionally, in order to achieve the aforementioned object, the present biometric identification apparatus is incorporated into another biometric identification apparatus with a vein imaging device in such a position that the present biometric identification apparatus does not interfere with the vein imaging device.

Additionally, in order to achieve the aforementioned object, the biometric identification apparatus of the present invention includes a fourth and a fifth light source, as well as display means. The fourth and the fifth light source for emitting light to a finger are disposed so that the optical axes of the fourth and the fifth light source form lines perpendicular to side surfaces perpendicular to the bottom surface of the finger placement portion. In addition, the third light source is disposed on the side surface to the left with respect to the direction in which the finger is placed in the finger placement portion, the fourth light source is disposed on the side surface to the right with respect to the direction in which the finger is placed in the finger placement portion, and the fifth light source is disposed in a position where the tip of the finger is located when the finger is placed in the finger placement portion. A difference of transmittance is obtained as the difference between the light intensity ratio of the light emitted from the third light source to the light detected with the receiver and the light intensity ratio of the light emitted from the fourth light source to the light detected with the receiver. The difference of transmittance thus obtained is compared with a previously-set threshold, and then the display means guides the finger in the right and left directions as well as in the horizontal direction. The transmittance; that is, the light intensity ratio of the light emitted from the fifth light source to the light detected with the receiver, is compared with a previously-set threshold, and then the display means guides the finger in a direction in which the finger is moved to touch the side surface.

EFFECTS OF THE INVENTION

According to the present invention, liveness detection on an object to be identified can be accurately and rapidly performed with a simpler structure than that of conventional technology, by obtaining the optical transmittance of an object to be identified and comparing the transmittance with a previously-set transmittance threshold.

DETAILED DESCRIPTION OF PREFERRED EMBODIMENTS OF THE INVENTION

Embodiment 1

FIG. 1 is an external view of a biometric identification apparatus 100 according to an embodiment of the present invention. Light sources 102 and 103, such as LEDs or lasers, are disposed on the bottom surface of a finger placement portion 101 on which a finger 200 for biometric identification is placed. The light sources 102 and 103 are disposed so that the optical axes thereof form lines perpendicular to the bottom surface of the finger placement portion 101. Receiving surfaces of receivers 104 and 105 such as photodiode devices are disposed parallel to the bottom surface of the finger placement portion 101. On side surfaces that are perpendicular to the bottom surface of the finger placement portion 101, there are disposed light sources 106, 107, and 108 such as LEDs or lasers, so that the optical axes thereof form lines perpendicular to the side surfaces of the finger placement portion 101. The optical axes of the light sources 102 and 103 are perpendicular to the optical axes of the light sources 106, 107, and 108. The receiving surfaces of the receivers 104 and 105 are parallel to the optical axes of the light sources 106, 107, and 108. Reference numeral 109 denotes a display unit for displaying results of detection. In FIG. 1, the biometric identification apparatus 100 is separate from the display unit 109. The display unit 109, however, may be formed integrally with the biometric identification apparatus 100. The principle of the biometric identification apparatus 100 will be described below.

FIG. 2 shows spectra of the human fingers (test subjects A and B) and spectra of an eraser, soap, a screw driver grip (transparent plastic) and acetal resin as materials for spoof fingers. These spectra are measured with the light sources 102 and 103 and the receivers 104 and 105 disposed on the bottom surface of the finger placement portion 101 shown in FIG. 1. In FIG. 2, the horizontal axis indicates wavelengths, and the vertical axis indicates transmittance; that is, the light intensity ratio of the light emitted to the light detected. By selecting a wavelength at which the difference between transmittance of the light passing through the test subjects and transmittance of the light passing through materials for spoof fingers is large, it becomes possible to discriminate a living body from a fake living body. Thus, in FIG. 2, we focused on wavelengths $\lambda 1$ (a in the figure) of a visible light region and wavelengths $\lambda 2$ (b in the figure) of a near-infrared light region. Namely, since the transmittance of the test subjects is 0% at $\lambda 1$ and the transmittance thereof is in the range of $X \pm a$ % at $\lambda 2$, the transmittance of the soap and acetal resin are out of the range at $\lambda 1$ and the transmittance of the soap, acetal resin, eraser and screw driver grip is out of the range at $\lambda 2$. Thus, a spoof finger can be accurately discriminated.

Meanwhile, vegetables or fruits may be fraudulently used as material for spoofing because of their components similar to those of a living body, namely, their large contents of water and sugar. FIG. 3 shows spectra of the test subjects, sweet potato, banana, and white radish. At $\lambda 1$ (a in the figure), it is possible to distinguish white radish from the test subjects, since transmittance of the white radish is sufficiently higher than those of the test subjects. In contrast, transmittance of banana is only slightly higher than those of the test subjects, and transmittance of sweet potato is equivalent (substantially 0%) to those of the test subjects. Further, at $\lambda 2$ (b in the figure), there is a wavelength region where only a small difference exists between the transmittance of the test subjects and the transmittance of the sweet potato, banana, and white radish. Accordingly, discrimination of these materials from the test subjects may be less accurate.

FIG. 4 shows spectra obtained by changing the way of emission of light with which the human finger, sweet potato, banana, and white radish are irradiated, so that the optical axes of the light sources are parallel to the receiving surface of the receivers. Specifically, the spectra are measured with the light sources 106 and 107 disposed on the side surfaces of the finger placement portion 101 and the receivers 104 and 105 shown in FIG. 1 Since the transmittance spectra in FIG. 4 for the test subjects, sweet potato, banana, and white radish have different shapes from those of FIGS. 1 and 3, and there is a wavelength range in a near-infrared light region where difference between the transmittance of sweet potato, banana and white radish and the transmittance of the test subjects is sufficiently large, it can be seen that discrimination can be carried out accurately in this wavelength range. Wavelengths $\lambda 3$ in the near-infrared light region, as denoted with c in the figure, are thus chosen in the present invention.

A combination of the aforementioned wavelengths $\lambda 1$ of the visible light region, the wavelengths $\lambda 2$ of the near-infrared region and the wavelengths $\lambda 3$ of the near-infrared region makes it possible to distinguish the human finger from the spoof finger with accuracy.

FIG. 5 is a flowchart for liveness detection with the biometric identification apparatus according to this embodiment. First, the light source (the light source 102 in FIG. 1) having the wavelengths $\lambda 1$ is caused to emit light (301), and the transmittance of an object is then measured with an output from the receiver (the receiver 104 or 105 in FIG. 1). Thereafter, determination is made by comparing the obtained transmittance with a previously-set threshold (e.g., 0%) of transmittance (302). When the obtained transmittance is out of the threshold, an alert (e.g., "No liveness detected") is displayed (303). When the transmittance is within the threshold, the light source (the light source 103 in FIG. 1) having the wavelengths $\lambda 2$ is caused to emit light (304), and the transmittance is then measured again with an output from the receiver (the receiver 104 or 105 in FIG. 1). Thereafter, determination is made by comparing the obtained transmittance with a previously-set threshold (e.g., $X \pm a$ %) of transmittance (305). When the obtained transmittance is out of the threshold, an alert (e.g., "No liveness detected") is displayed (303). When the transmittance is not out of the threshold, the light source (the light source 106 or 107 in FIG. 1) having the wavelengths $\lambda 3$ is caused to emit light (306), and the transmittance is then measured for the third time with an output from the receiver (the receiver 104 or 105 in FIG. 1). Thereafter, determination is made by comparing the obtained transmittance with a previously-set threshold (e.g., $Y \pm \beta$ %) of transmittance (307). When the obtained transmittance is out of the threshold, an alert (e.g., "No liveness detected") is displayed (303). When the transmittance is not out of the threshold, the result of the determination (e.g., "Liveness detection complete") is displayed (308). As described above, in the liveness detection of the present invention, since it is only necessary to determine whether or not the detected transmittance is within the predetermined threshold, circuitry can be made simpler than a conventional circuitry for processing images, and the determination can be made within a shorter period of time. Moreover, the configuration of the apparatus for carrying out the liveness detection can be made simple, as the apparatus only needs the light sources and the receivers placed in the finger placement portion. Additionally, it is preferable that these components be controlled with a microcomputer. Accordingly, reliability can be improved at low cost and time required can be reduced.

Embodiment 2

FIG. 6 shows an embodiment in which the biometric identification apparatus of the present invention is incorporated into biometric identification by fingerprint imaging. A fingerprint imaging unit 130 is incorporated into the bottom surface of a finger placement portion 101 of a biometric identification apparatus 120, so that the fingerprint imaging unit 130 does not interfere with the light sources 102, 103, 106, 107, and 108, and the receivers 104 and 105. Identification is made by first placing a finger in the finger placement portion 101, and then by performing determination of liveness detection. Thereafter, by drawing the finger back while lightly pressing the finger against the bottom surface of the finger placement portion 101, an image of the fingerprint can be obtained with the finger print imaging unit 130. In FIG. 6, while the biometric identification apparatus 120 and a display unit 109 are separate from each other, the display unit 109 may be integral with the biometric identification apparatus 120.

Embodiment 3

FIG. 7 shows an embodiment in which the biometric identification apparatus of the present invention is incorporated into biometric identification by vein imaging. A vein imaging unit 150 is incorporated into the bottom surface of a finger placement portion 101 of a biometric identification apparatus 140, so that the vein imaging unit 150 does not interfere with the light sources 102, 103, 106, 107, and 108, and the receivers 104 and 105. Moreover, as light sources for imaging veins, imaging light sources 110 are incorporated into a surface perpendicular to the surface where the vein imaging unit 150 is located. Identification is made by first placing a finger in the finger placement portion 101, and then by performing determination of liveness detection. Thereafter, the imaging light sources 110 are caused to emit light in a state where the finger remains placed on the finger placement portion 101. Thus, an image of the veins of the finger is obtained with the vein imaging unit 150. In FIG. 7, while the biometric identification apparatus 140 and a display unit 109 are separate from each other, the display unit 109 may be integral with the biometric identification apparatus 140.

Embodiment 4

In biometric identification, there are cases of failing to verify an authorized individual (false rejection) or of incorrectly verifying an unauthorized individual (false acceptance). In order to increase the accuracy of authentication, it is important that a photographed image; that is, biometric information, be stably obtained with uniform quality, and it is necessary that the finger be placed in a predetermined posture. Thus, a method for detecting a finger posture will be described below, the method using the light sources 106, 107, and 108 disposed on the side surfaces of the finger placement portion 101, and the receiver 104 or 105 disposed on the bottom surface of the finger placement portion 101 shown in FIG. 1.

FIG. 8 is a plan view showing a state in which a finger 200 is placed in a finger placement portion 101 as viewed from above, and showing a state in which a finger 200 is placed to the left side. In this state, the transmittance of the light emitted from the light source 106 placed on the left-hand side and detected with the receiver 104 or 105 is lower than the transmittance of the light emitted from the light source 107 placed on the right-hand side and detected with the receiver 104 or 105.

In contrast, FIG. 9 shows a state in which the finger 200 is placed to the right side. This case is opposite the case of FIG. 8, and the transmittance of the light emitted from the light source 106 placed on the left-hand side and detected with the receiver 104 or 105 is higher than the transmittance of the light emitted from the light source 107 placed on the right-hand side and detected with the receiver 104 or 105.

FIG. 8 shows a case in which the finger 200 is placed to the left on a horizontal plane, and FIG. 9 shows a case in which the finger 200 is placed to the right on a horizontal plane. However, there are also cases in which the finger 200 may be tilted either to the right or to the left. FIG. 10 is a rear view of the finger 200 being tilted toward the light source 106. In this state, as in the case of FIG. 8, the transmittance of the light emitted from the light source 106 and detected with the receiver 104 or 105 is smaller than the transmittance of the light emitted from the light source 107 opposite to the light source 106 and detected with the receiver 104 or 105. In contrast, FIG. 11 shows a rear view of the finger 200 being tilted toward the light source 107. In this state, as in the case of FIG. 9, the transmittance of the light emitted from the light source 106 and detected with the receiver 104 or 105 is larger than the transmittance of the light emitted from the light source 107 opposite to the light source 106 and detected with the receiver 104 or 105.

While the method for detecting the position of a finger in the right and left directions on a horizontal plane and the method for detecting the tilt of a finger have been described with reference to FIGS. 8 to 11, it is also important to determine whether or not a finger tip is placed at the tip end of the finger placement portion 101. As shown in FIG. 12, using the light source 108 disposed on a side surface at the center of the tip of the finger placement portion 101, determination is made based on the transmittance detected with the receiver 104 or 105. The figure shows a state in which the finger 200 is not in contact with the tip end of the finger placement portion 101. In this case, the transmittance of the light emitted from the light source 108 and detected with the receiver 104 or 105 is smaller than a certain threshold (the transmittance in a state in which the finger 200 is in contact with the tip end of the finger placement portion 101).

FIG. 13 is a flowchart for guiding the finger to be in a predetermined posture by determining a state in which the finger is placed. First, the light sources (the light sources 106, 107, and 108) having the wavelengths λ3, which are respectively placed in the right, left and center side surfaces of the finger placement portion 101, are caused to emit light (401). Then, the transmittance of an object is measured based on an output from the receiver (the receiver 104 or 105). First, determination is made by comparing, with a previously-set threshold, the difference between the transmittances of the lights emitted from the light sources in the left and right side surfaces (the light sources 106 and 107) (402). When the difference of transmittance is out of the threshold, an alert (e.g., "Correctly place finger sidewise and horizontally") is displayed (403), and the flow returns to 401. On the other hand, when the difference of transmittance is within the threshold, determination is made by comparing the transmittance of the light emitted from the center side surface (the light source 108) with a previously-set threshold (404). When the difference of transmittance is out of the threshold, an alert (e.g., "Move finger toward the tip end") is displayed (405), and the flow returns to 401. On the other hand, when the difference of transmittance is within the threshold, the flow proceeds to a sequence for liveness detection (406) shown in FIG. 5. Accordingly, the finger 200 can be placed correctly in the finger placement portion 101, and thereby biometric identification (liveness detection and imaging of fingerprint, veins or the like) can be performed accurately. Additionally, it is preferable that these components be controlled with a microcomputer. Accordingly, reliability can be improved at low cost, and time required can be reduced.

It should be noted that each threshold may be given by a formula with parameters of a plurality of wavelengths, instead of the above-described fixed value.

EXPLANATIONS OF LETTERS OR NUMERALS

Figure 1:
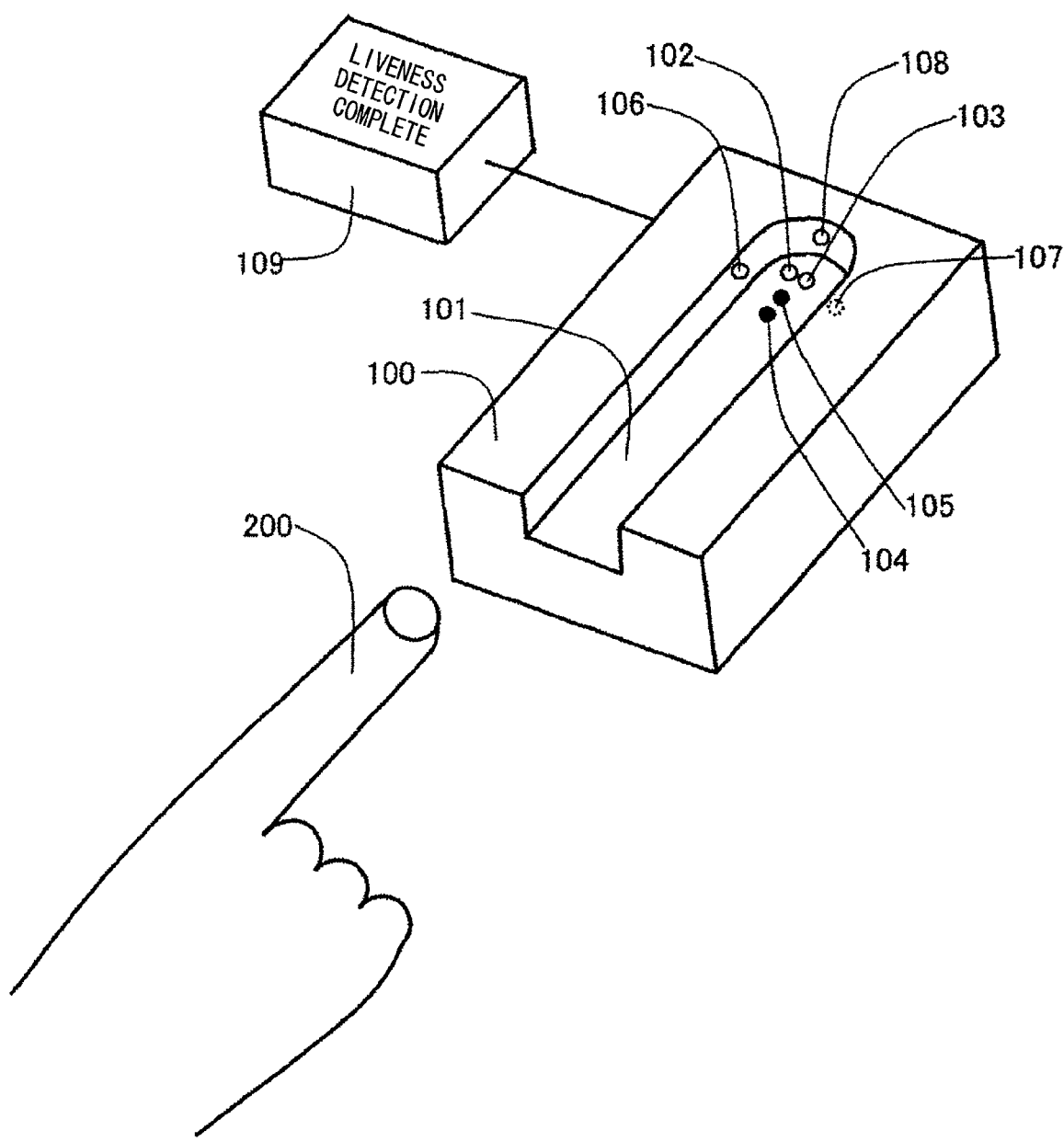
FIG. 1 is an external view of a biometric identification apparatus showing a first embodiment of the present invention.
Figure 2:
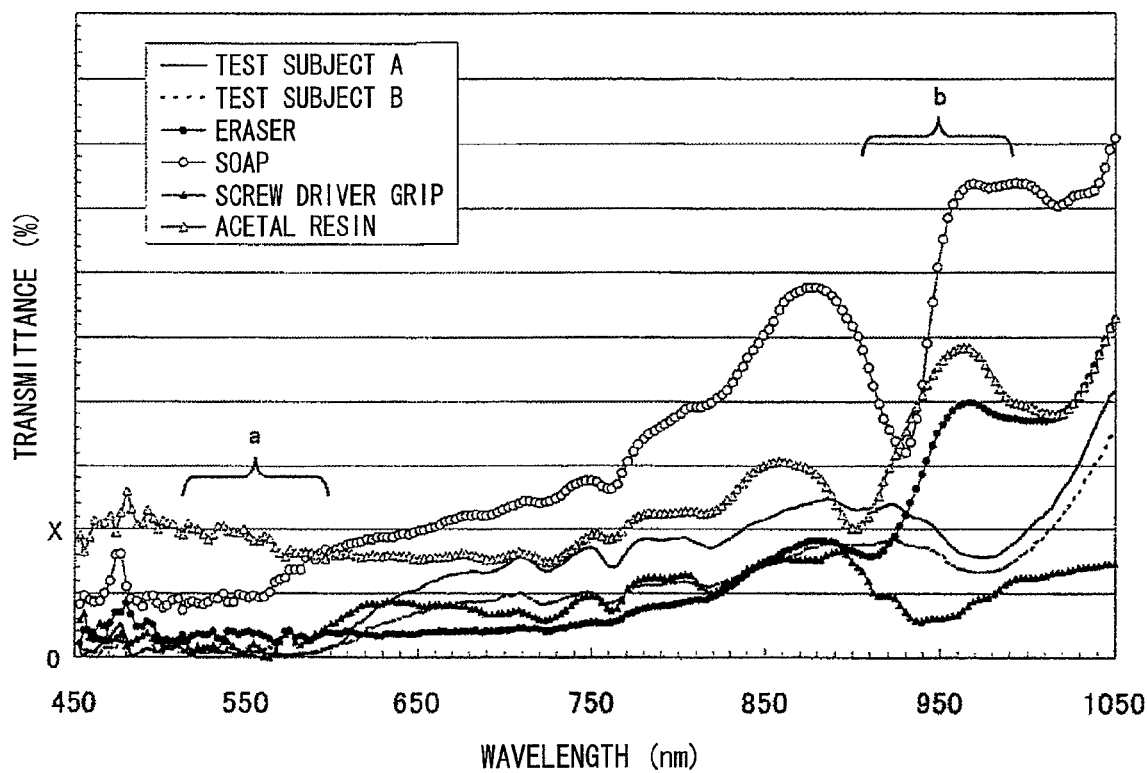
FIG. 2 is a diagram showing spectra of test subjects and materials for spoof fingers.
Figure 3:
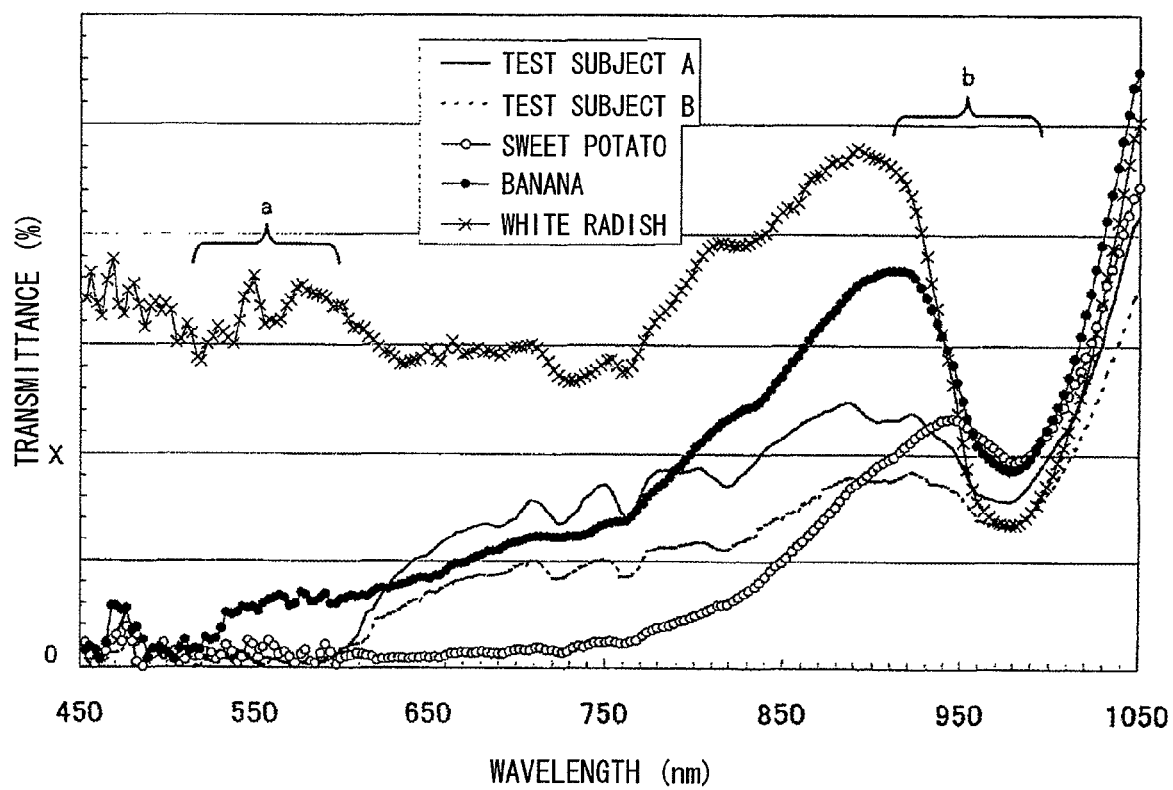
FIG. 3 is a diagram showing spectra of test subjects, sweet potato, and banana.
Figure 4:
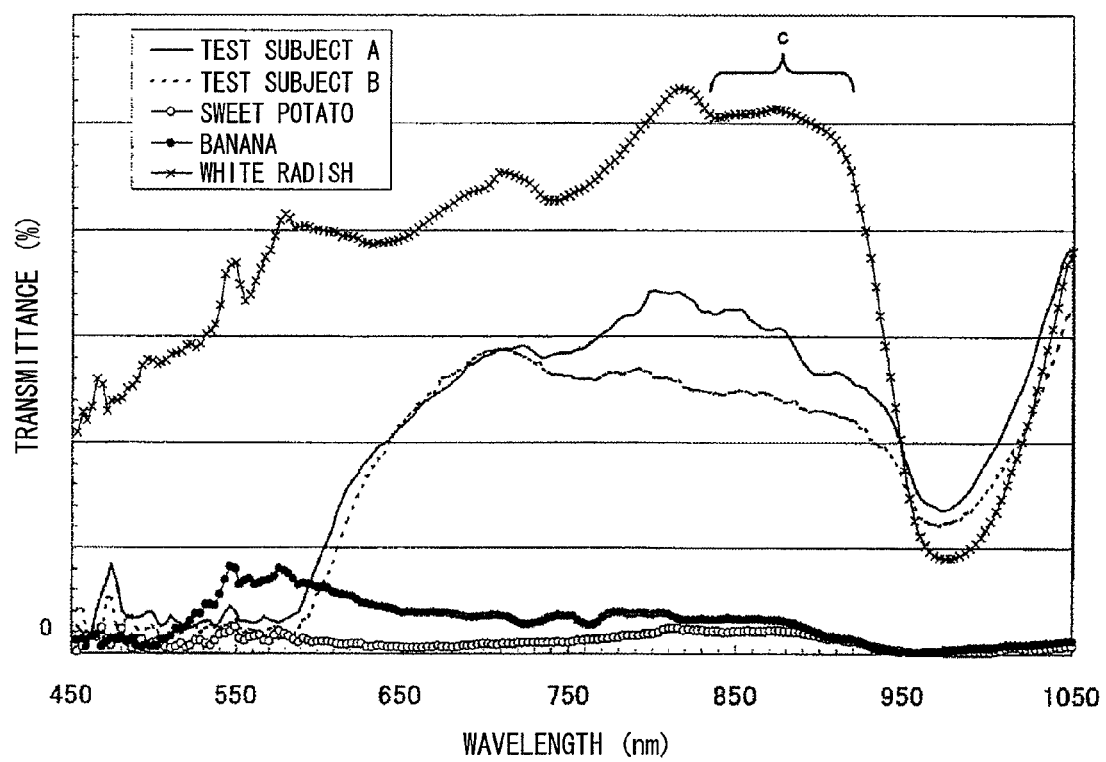
FIG. 4 is a diagram showing spectra of test subjects, sweet potato, and banana.
Figure 5:
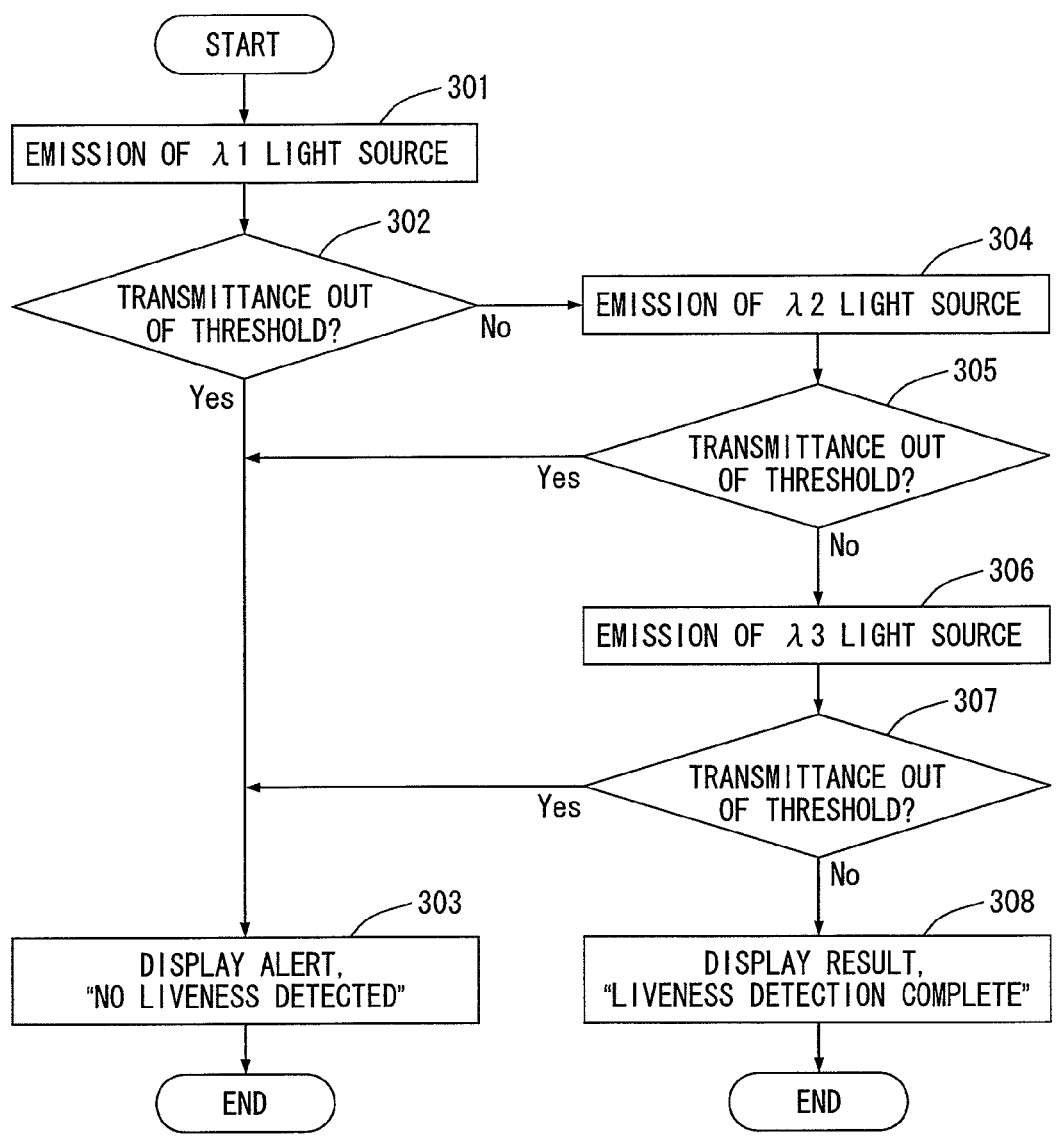
FIG. 5 is a flowchart for liveness detection with the biometric identification apparatus according to the embodiment.
Figure 6:
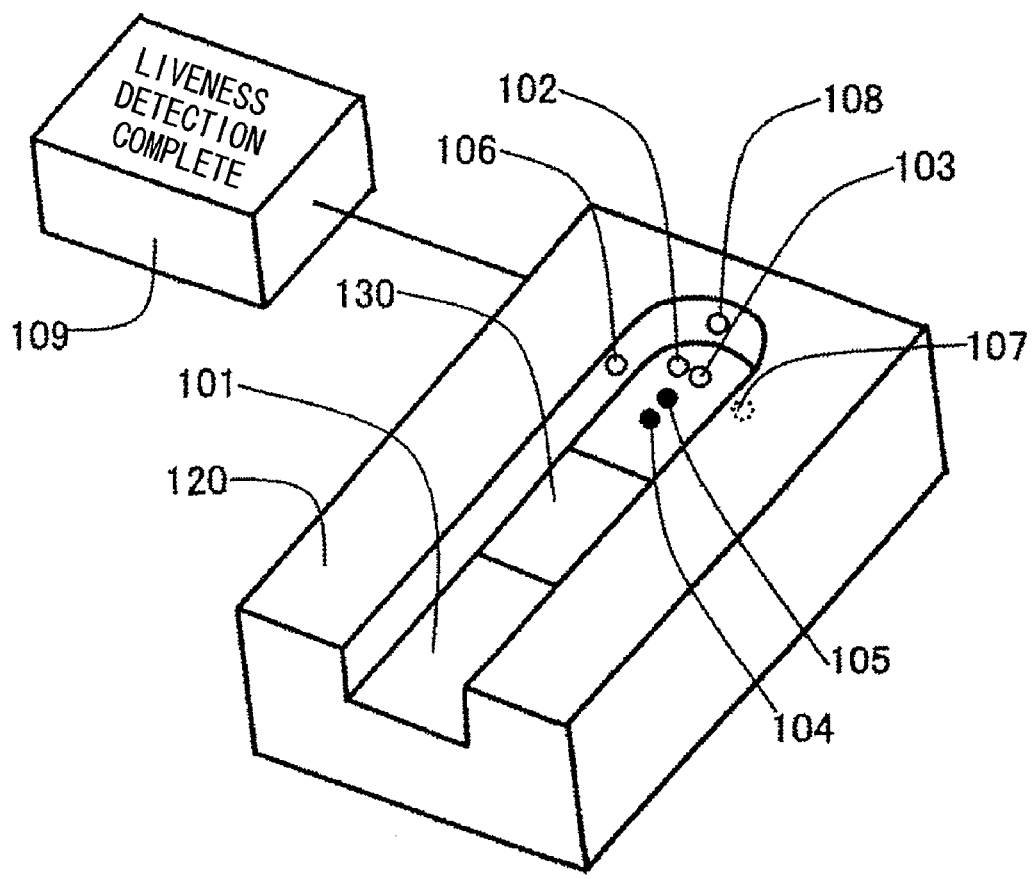
FIG. 6 is an external view of a biometric identification apparatus showing a second embodiment of the present invention.
Figure 7:
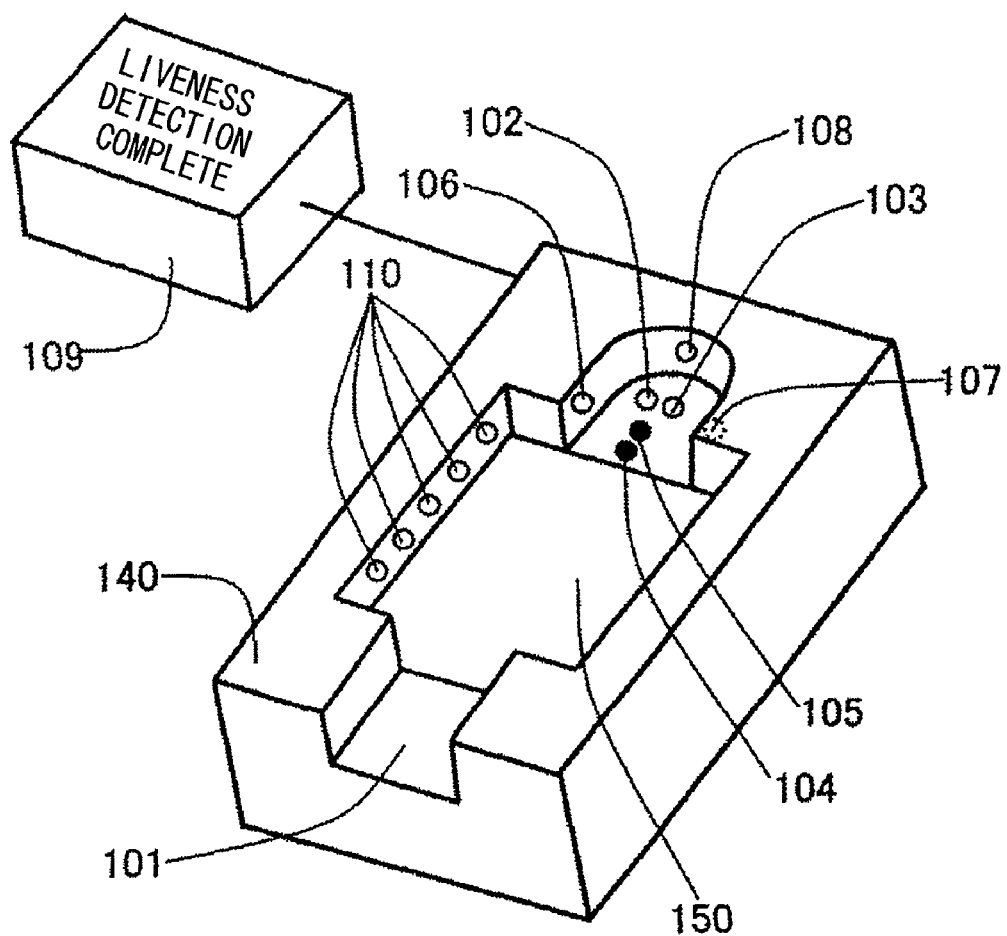
FIG. 7 is an external view of a biometric identification apparatus showing a third embodiment of the present invention.
Figure 8:
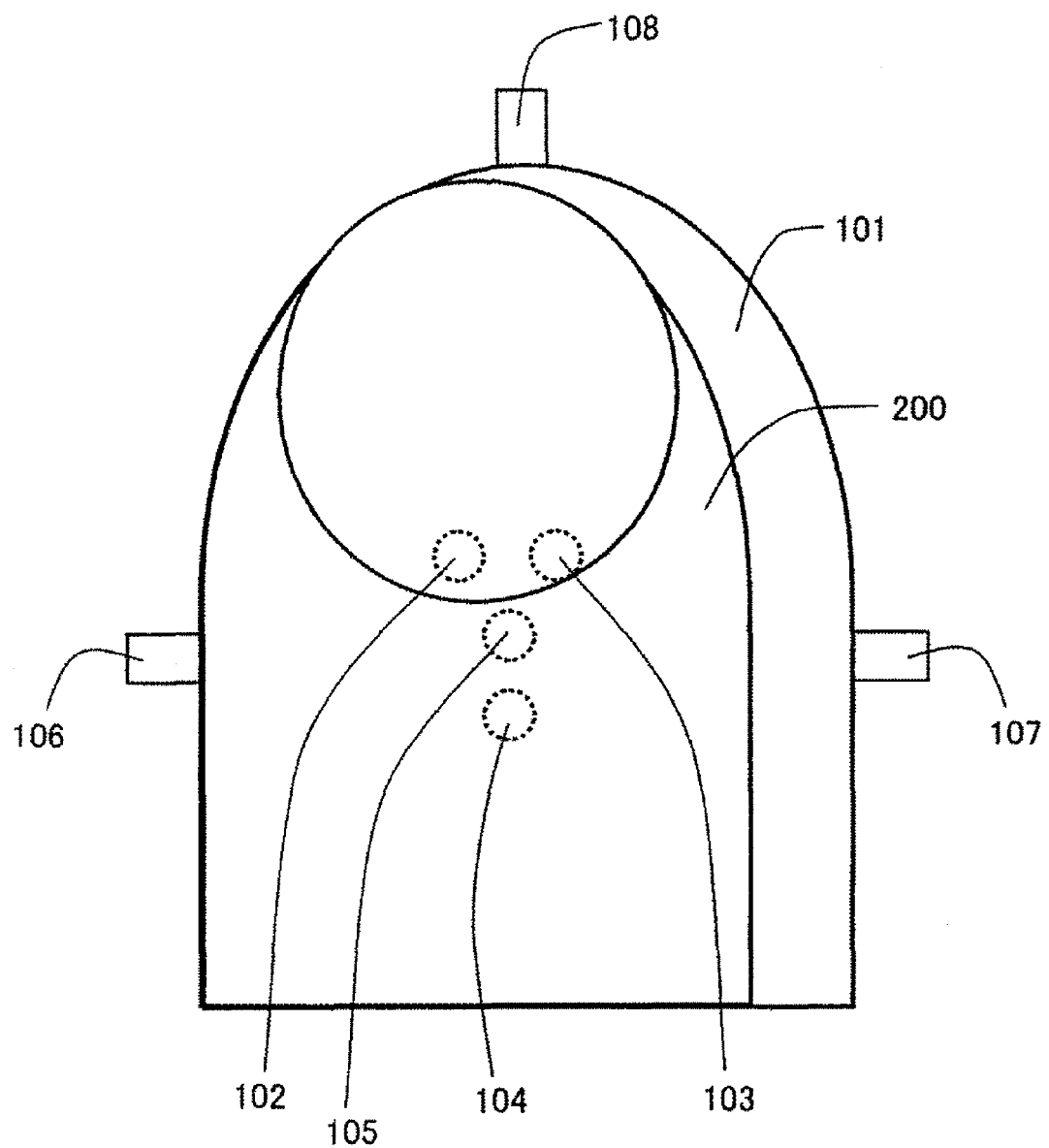
FIG. 8 is a plan view of a state in which a finger is placed in a finger placement portion as viewed from above.
Figure 9:
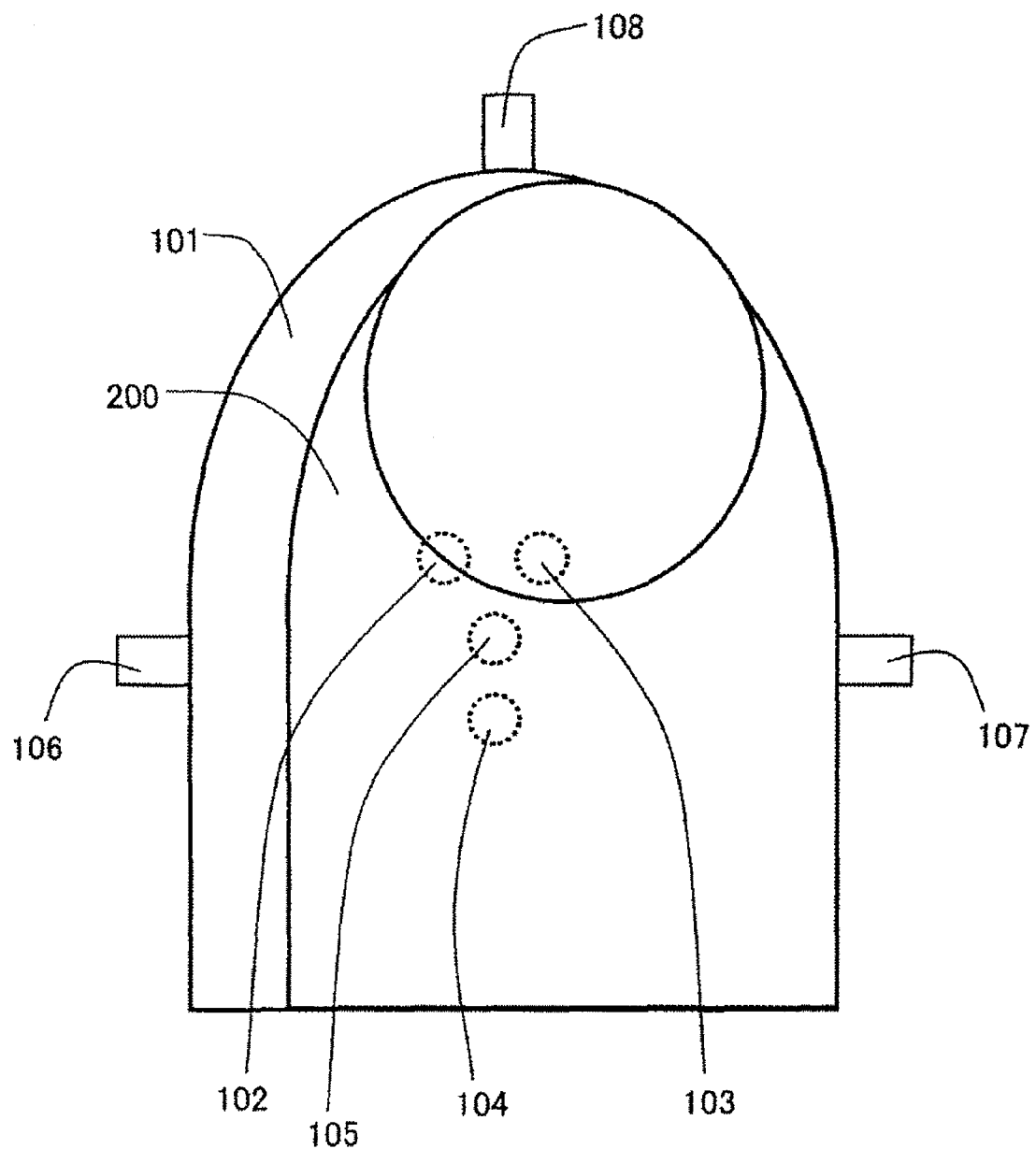
FIG. 9 is a plan view of a state in which a finger is placed in a finger placement portion as viewed from above.
Figure 10:
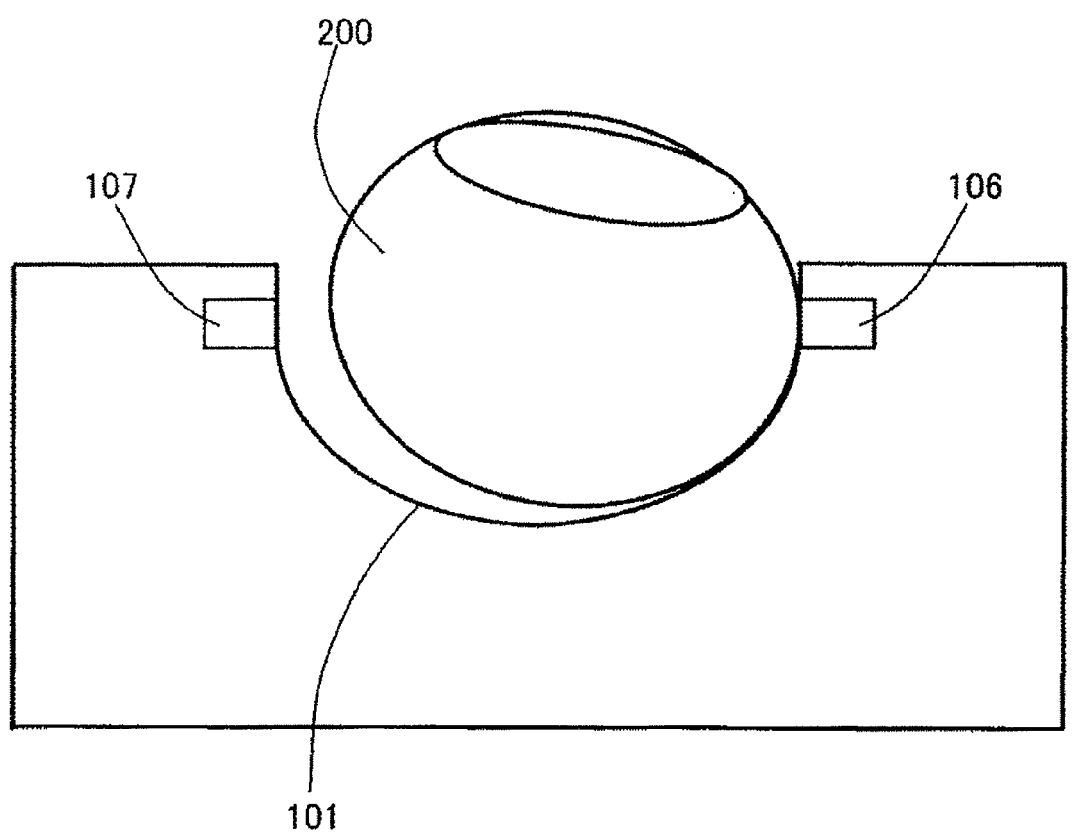
FIG. 10 is a rear view of the apparatus when the finger is tilted.
Figure 11:
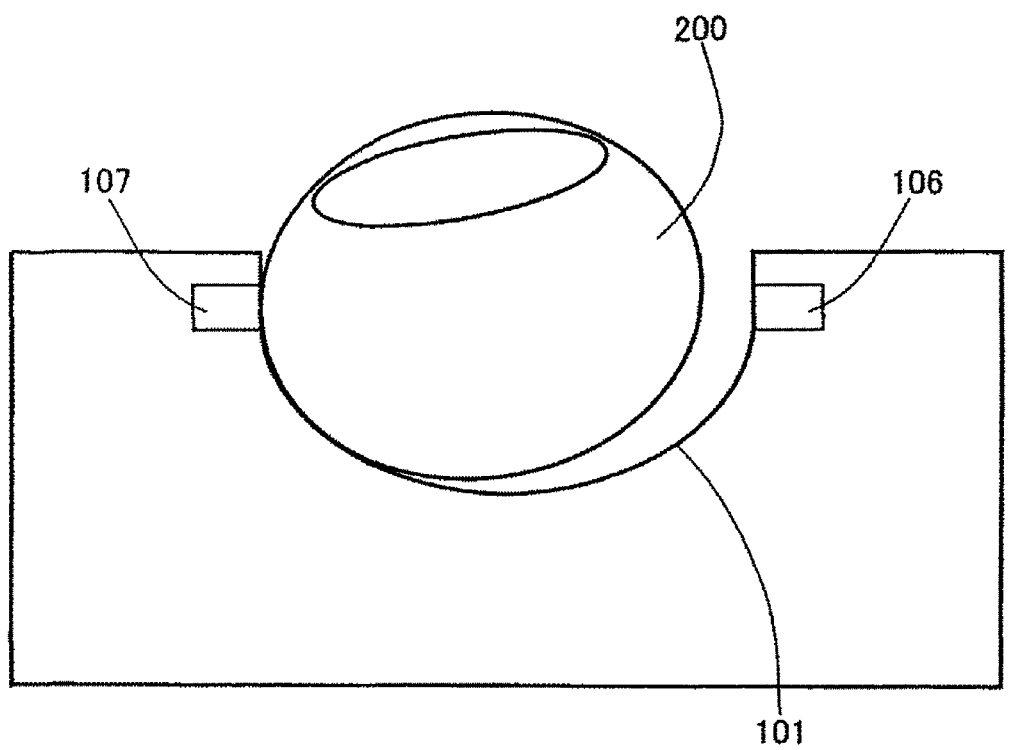
FIG. 11 is a rear view of the apparatus when the finger is tilted.
Figure 12:
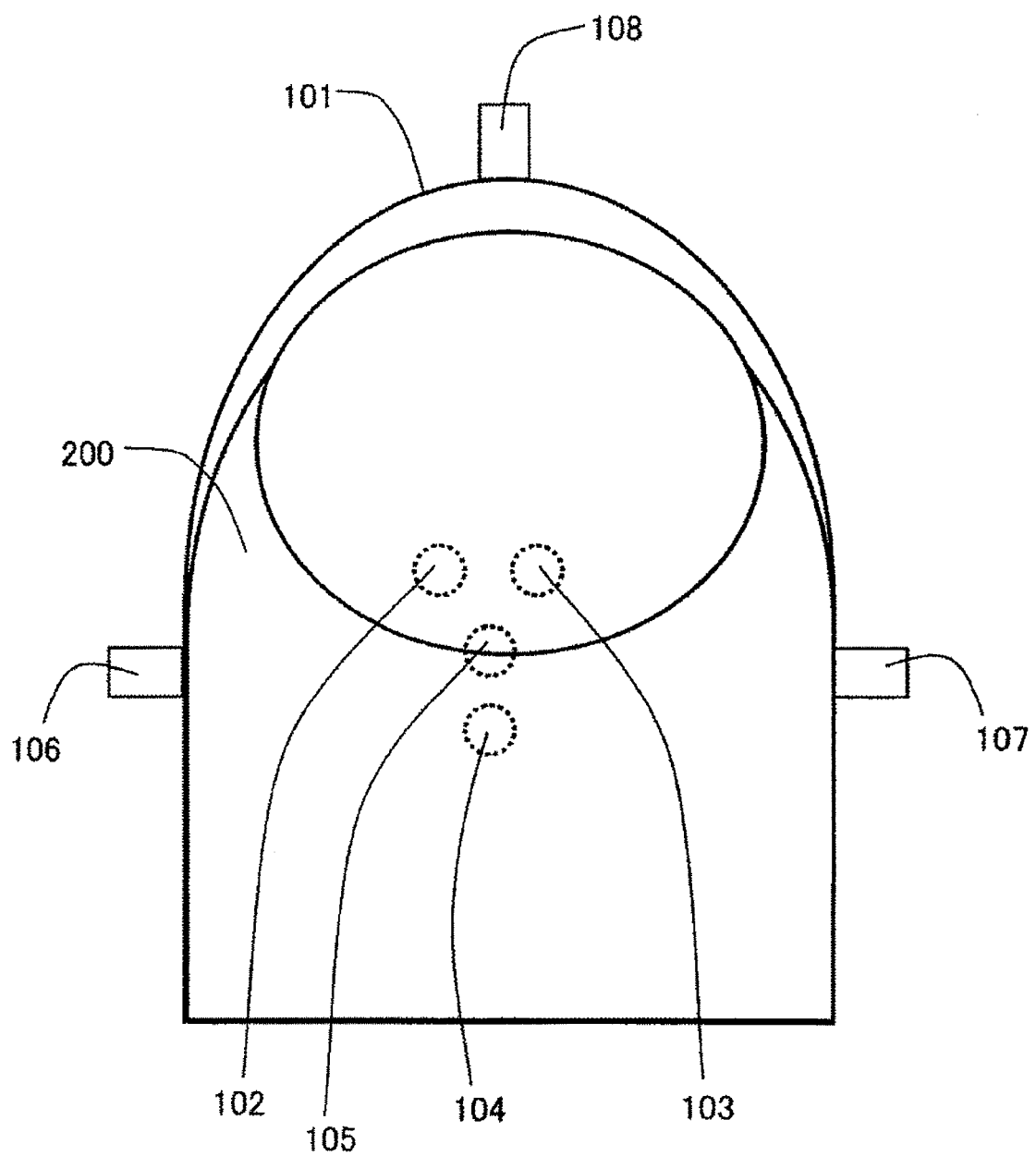
FIG. 12 is a plan view of a state in which a finger is placed in the finger placement portion as viewed from above.
Figure 13:
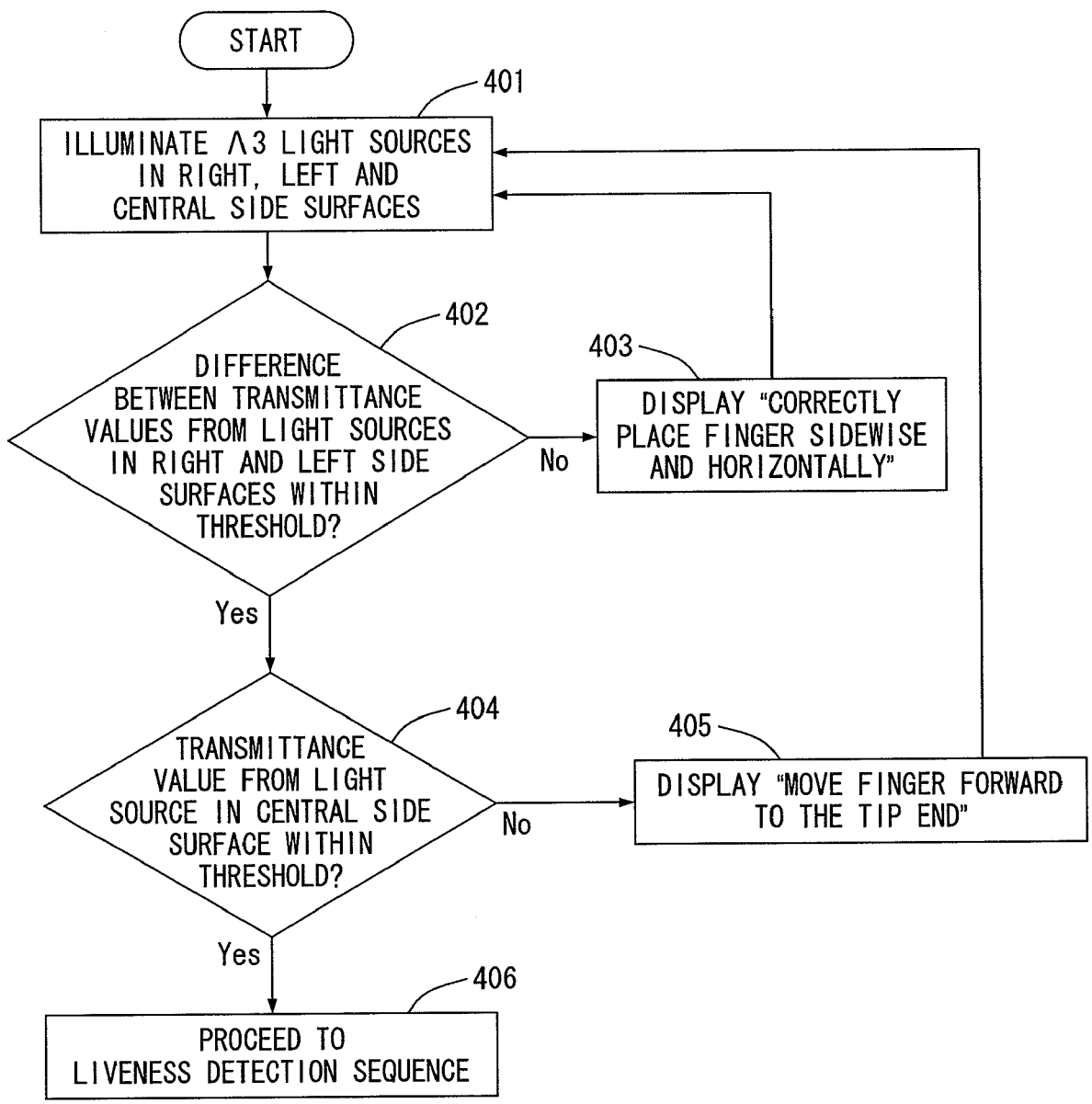
FIG. 13 is a flowchart for determining a state in which the finger is placed and guiding the finger to be in a predetermined posture.

100, 120, 140 . . . biometric identification apparatus, 101 . . . finger placement portion, 102, 103, 104, 105, 106, 107, 108 . . . light sources, 109 . . . display unit, 110 . . . imaging light sources, 130 . . . finger print imaging unit, 150 . . . vein imaging unit, 200 . . . finger, 301, 304, 306, 401 . . . light source emission, 302, 305, 307, 404 . . . determination of transmittance based on threshold, 303 . . . display of alert, 308 . . . display of results, 402 . . . comparison between difference of transmittance and threshold, 403, 405 . . . display.

The invention claimed is:

1. A biometric identification apparatus comprising:
   a finger placement portion in which a finger is placed;
   a first, a second and a third light source having different wavelengths from one another for emitting light to the finger; and
   a receiver for detecting the light passing through the finger;
   wherein the first and the second light source are disposed so that the optical axis of the first light source and that of the second light source form lines perpendicular to the bottom surface of the finger placement portion;
   wherein the third light source is disposed so that the optical axis of the third light source is parallel to the bottom surface of the finger placement portion and is perpendicular to the optical axis of the first light source and that of the second light source;
   wherein a receiving surface of the receiver is disposed parallel to the bottom surface of the finger placement portion; and
   wherein a transmittance; that is, a light intensity ratio of the light emitted from each of the first, the second and the third light source to the light detected with the receiver, is obtained the transmittance is compared with respective previously-set thresholds of transmittance, to detect whether or not the finger is a living body, and a detection result is displayed.

2. The biometric identification apparatus as recited in claim 1, wherein the wavelengths of the first, the second and the third light source include a visible light region and a near-infrared light region.

3. A biometric identification apparatus, comprising:
   a fingerprint or vein imaging device for obtaining biometric information, the apparatus further comprising the biometric identification apparatus as recited in claim 1 incorporated in a position such that it does not interfere with the imaging device.

4. The biometric identification apparatus as recited in claim 1, further comprising:
   a fourth and a fifth light source for emitting light to the finger; and
   display means;
   wherein the fourth and the fifth light source are disposed so that the optical axis of the fourth light source and that of the fifth light source form lines perpendicular to side surfaces perpendicular to the bottom surface of the finger placement portion;
   wherein the third light source is disposed on the side surface to the left with respect to the direction in which the finger is placed in the finger placement portion;
   wherein the fourth light source is disposed on the side surface to the right with respect to the direction in which the finger is placed in the finger placement portion;
   wherein the fifth light source is disposed in a position where the tip of the finger is located when the finger is placed in the finger placement portion;
   wherein the display means compares a previously-set threshold with a difference of another transmittance; that is, a difference between a light intensity ratio of the light emitted from the third light source to the light detected with the receiver and a light intensity ratio of the light emitted from the fourth light source the light detected with the receiver, so as to guide the finger in the right and left directions as well as in the horizontal direction; and
   wherein the display means also compares a previously-set threshold with a further transmittance; that is, a light intensity ratio of the light emitted from the fifth light source to the light detected with the receiver, so as to guide the finger in a direction in which the finger is moved to touch the side surface.

* * * * *